United States Patent [19]

Marett

[11] Patent Number: 5,685,319

[45] Date of Patent: Nov. 11, 1997

[54] METHOD AND APPARATUS FOR DETERMINING THE FERTILITY STATUS OF WOMEN

[76] Inventor: Douglas Michael Marett, 1481 Queens Street East, Toronto, Ontario, Canada, M4L 1E2

[21] Appl. No.: 573,783

[22] Filed: Dec. 18, 1995

[51] Int. Cl.⁶ .................................................. A61B 10/00
[52] U.S. Cl. ........................................................ 128/738
[58] Field of Search ............................... 128/736, 738, 128/897–898, 65, 632, 635

[56] References Cited

U.S. PATENT DOCUMENTS

| | | | |
|---|---|---|---|
| 4,010,738 | 3/1977 | Preti et al. | 128/738 |
| 4,582,589 | 4/1986 | Ushizawa et al. | 204/433 |
| 4,653,499 | 3/1987 | Murray, Jr. et al. | 128/635 |
| 4,814,060 | 3/1989 | Banks | 204/406 |
| 4,879,294 | 11/1989 | Cutler et al. | 436/65 |
| 4,931,403 | 6/1990 | Cutler et al. | 436/65 |
| 5,050,604 | 9/1991 | Reshef et al. | 128/635 X |
| 5,133,856 | 7/1992 | Yamaguchi et al. | 204/416 |
| 5,155,045 | 10/1992 | Cutler et al. | 436/65 |
| 5,467,778 | 11/1995 | Cott et al. | 128/738 |

*Primary Examiner*—Francis Jaworski
*Attorney, Agent, or Firm*—Henderson & Sturm

[57] ABSTRACT

A method and apparatus for predicting the fertility status of a human female subject. The onset of menstruation of the subject is noted. Daily determinations are made of the subjects eccrine sweat pH, beginning not more than 4 days following menstruation. The start of the fertile period is determined as a function of a significant decline in pH, followed by a sharp rise. The peak of this pH rise is indicative of imminent ovulation, which generally coincides with a second pH decline of variable degree. The apparatus provides provisions for automatically taking the pH readings, analysing them, and displaying to the user the daily fertility status.

17 Claims, 5 Drawing Sheets

METHOD AND APPARATUS FOR DETERMINING THE FERTILITY STATUS OF WOMEN

FIELD OF THE INVENTION

The present invention relates to a method and apparatus for the determination of fertility status during the menstrual cycle of a human female. More specifically, the invention relates to a method and apparatus for the accurate determination of the fertile phase from the non-fertile phase of the menstrual cycle of the human female, as well as the most likely day of ovulation.

BACKGROUND OF THE INVENTION

Ovulation is the central event of the reproductive cycle. During an average 28 day cycle in humans, a released egg survives only about 12–24 hours, making the fertile window relatively narrow. However, the uteris is capable of storing sperm for up to four days. Thus the actual fertile phase is about 4 days prior to ovulation to 1 day after.

In humans, the maturation of ovarian follicles which will eventually release a fertile egg are effected by the action of Follicle Stimulating Hormone (FSH) and Luteinizing Hormone (LH) secreted by the anterior lobe of the pituitary. The ovulatory phase of the menstrual cycle is preceded by a significant rise in serum total estrogens 24–48 hours prior to ovulation, which prepare the uterus for possible implantation. The rise in estrogens is followed by a rapid rise in serum luteinizing hormone reaching a peak 12–24 hours prior to ovulation. Many other physiological conditions also change around the time of ovulation. Basal body temperature (BBT) reaches a nadir followed by a sharp rise around the time of ovulation. Cervical mucus undergoes viscosity changes stimulated by rising estrogen which can help direct sperm towards the egg.

Several fertility detectors have been developed which measure these various hormones or their indirect physiological effects. The BBT method generally requires a women to take her vaginal temperature every morning before rising and chart the value. Besides the considerable diligence involved, the method is generally only accurate within ±2 days of ovulation, and gives no prior notice. Cervical mucus measurements have been regarded as somewhat more helpful. Women can examine their cervical mucus for the spinbarkeit reaction, which is a thinning of the mucus just before ovulation which allows it to be drawn intact between the fingers. Another method involves examining the cervical mucus under a microscope and looking for a "ferning" reaction indicative of immenent ovulation. A third method uses the measurement of vaginal mucus conductivity using impedance probes which allows a somewhat more quantitative estimation of the mucus changes (U.S. Pat. No. 4,770,186). However, cervical mucus examination suffers from subjective errors as well as being arduous and again gives little to no prior notice of ovulation.

Fertility detectors based on the measurement of urinary estrogens and in particular, LH have become widespread and are considered highly accurate. However, these assays require considerable diligence for home use and none of these detectors are capable of giving accurate predictions of impending ovulation more than 24–48 hours ahead of time, thus making them unsuitable for use as a form of birth control.

There is a need for an accurate method of predicting ovulation at least 4 days ahead of time. By identifying for each user the period during which she is fertile, women wishing to avoid becoming pregnant would be able to plan contraception more effectively. Further, such a device would be suitable for planning pregnancy, since it would identify the most fertile days of the cycle including the most likely day of ovulation, and give plenty of notice to the user. Such a device should be automatic, thus being able to take readings without user manipulation, yet be inocuous.

SUMMARY OF THE INVENTION

The present invention provides a method and apparatus for accurately determining the fertility status of a human female. It also provides a method and apparatus for predicting the most likely day of ovulation at least 4 days in advance. The method involves essentially measuring the pH of the subjects eccrine sweat on the surface of the skin, and by observing the pattern of peaks and troughs in the daily pH readings, predicting the fertile period and imminent day of ovulation. The apparatus utilized involves a means for sensing the pH of a womans eccrine sweat together with an means for indicating the pH values. The values may be either plotted manually, or may be read automatically by a microprocessor, which is programmed to take readings at regular intervals and store them to memory. When performed in conjuction with a microprocessor, there is provided a means of automatically analysing the stored data using software algorithms to provide an accurate prediction of the fertility status of the woman.

DETAILED DESCRIPTION OF THE INVENTION

The present invention involves a simple method that has been developed whereby the fertile period preceeding ovulation as well as the ovulation event itself can be predicted and accurately identified in the human female. This method results in a reliable self-monitoring personal use test. It can also be used by a physician in the treatment of female infertility since many diagnostic or therapeutic measures depend on the accurate prediction and detection of ovulation. The method futher lend itself to this task due to the relative ease of measuring eccrine sweat pH values. Eccrine sweat is a thin watery fluid which is secreted onto the surface of human skin by the eccrine sweat glands. The thick skin such as the palms is abundantly supplied by eccrine sweat glands, but they are also found in substantial numbers in thin skin. Eccrine sweat secretions are complex systems containing several electrolytes including sodium (30–150 mmol), potassium (10–40 mmol) and chlorine (40–110 mmol). It also contains non-electrolyte components such as lactate, urea, glucose, protein, free amino acids, and lipids ( Hadi, et.al. Eur. J. Clin. Chem. Clin. Biochem. 1994, Vol. 32, pp.71–77). It has been determined that the pH of human eccrine sweat is somewhat acidic in the pH 4–6 range and that the lactic acid-lactate system is responsible for the main pH buffering capacity of sweat (Anton'ev, A. A., et.al. Vestn.

Dermatol. Verereol (1978),10:6.). However, I have found that the predominant acid components of eccrine sweat represent a small group of compounds. These acidic compounds are responsible for greater than 90% of the acidity of eccrine sweat, and appear to be released in a pattern linked with ovulation. It is believed that one or more of these acidic compounds serve a hormonal function, and may act horizontally between humans. Although variability does exist in the average eccrine sweat pH from woman to woman, the pattern of eccrine sweat pH change is consistent and can be easily analysed by a subject or a by a computer programmed to recognize the pattern. Thus an identical instrument can be used by all subjects without adjustment or individual calibration.

Figure 1:
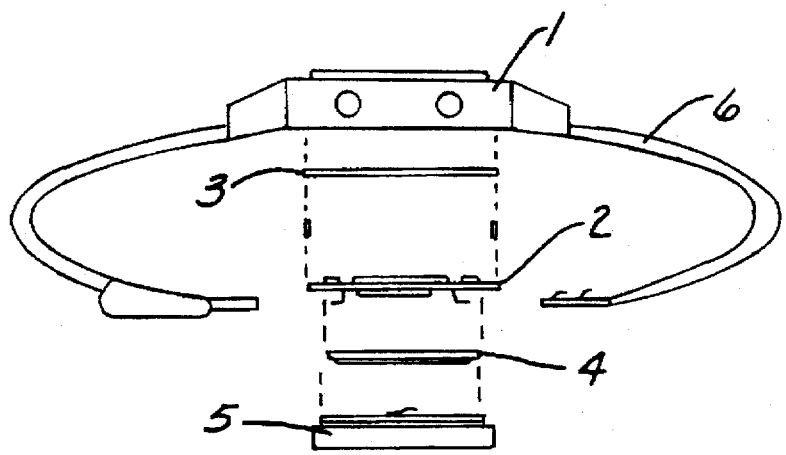
FIG. 1 is a exploded view of an apparatus using a microprocessor for indicating fertility status in accordance with the present invention.
Figure 2:
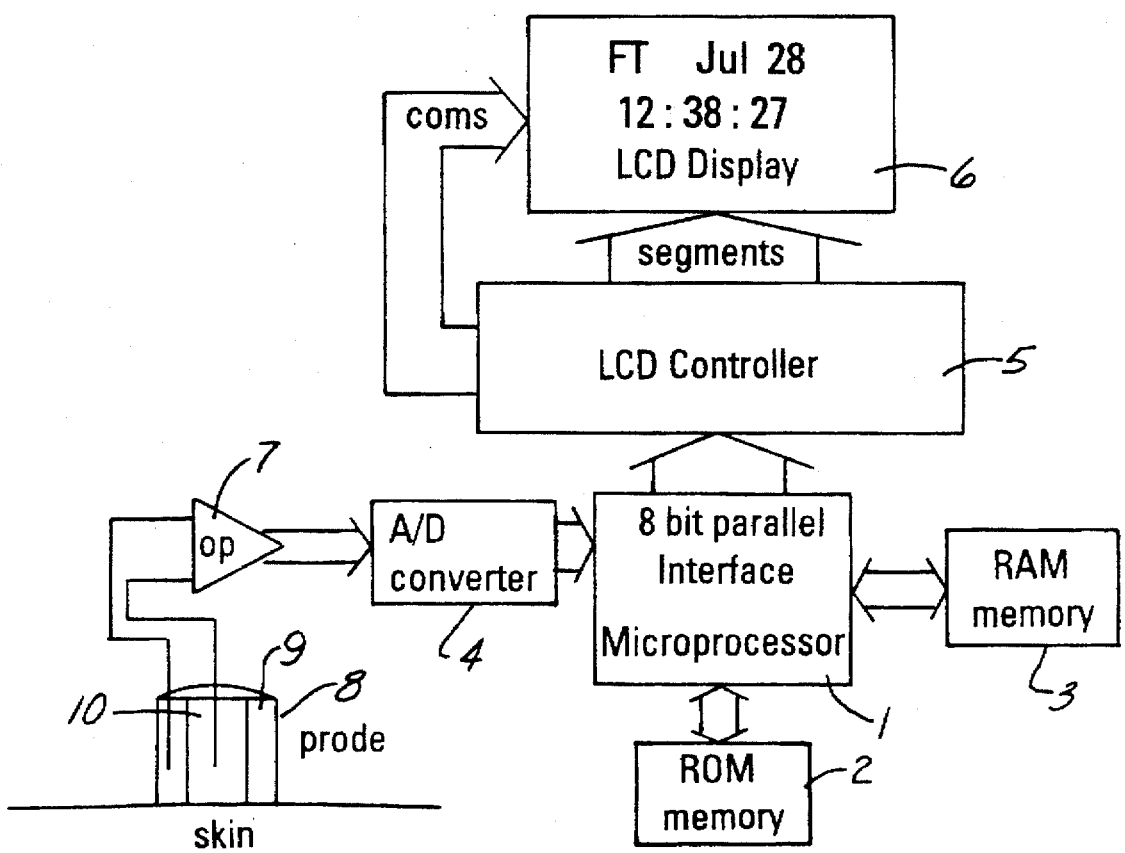
FIG. 2 is a block flow diagram of apparatus using a microprocessor for indicating fertility status in accordance with the present invention.

Using the present method, a user is able to predict the onset of her fertile period and time of ovulation. To this end, the pH of the subjects eccrine sweat, usually measured directly on the surface of the skin, is monitored periodically, preferably once or several times daily, with an instrument designed for that purpose. Alternatively, the eccrine sweat may be collected from the skin and its pH read. Readings are typically taken by placing the pH sensing element of the device on the surface of the womans skin, such as on the lower arm or hand region. If the skin is very dry, a sparse amount of distilled water may be applied and rubbed in to provide a more stable reading. After stabilization a reading is taken, and recorded for later plotting. If necessary several readings may be taken and averaged. If the device is intended to be worn, such as like a watch, then it is affixed to the wrist or arm by a band or similar implement with the sensor surface contacting the skin surface. The sensor is designed to be flat and of as large a surface are as possible so that when worn snuggly against the skin it promotes sweating and retention of sweat. If computer controlled, at periodic intervals the built-in microprocessor takes a reading from this sensor, which has its pH-indicating and reference elements bridged by this retained sweat. The microprocessor then automatically stores the read value to its temporary memory. Basically, one illustrative instrument, shown in FIG. 1 and described in more detail below consists of a housing 1 containing an electronic printed circuit board 2, a digital display 3, a power source 4, and a pH sensing element 5 which makes contact with the skin surface via the tightening of a wrist strap 6. The block diagram for this device is shown in FIG. 2. The microprocessor 1 operates by a software routine held in the ROM memory 2. This routine counts time in seconds, hours, days, and months, and serves as the timebase for the entire unit. The time is displayed via an LCD controller 5 which drives and appropriate LCD display 6. A pH sensing probe 8 consisting of a pH-indicating electrode 10 and an attached reference electrode 9 are positioned in such a manner that they are constantly in contact with the users wrist while the device is being worn. The voltage difference between the sensing electrode 10 and the reference electrode 9 are amplified by an operational amplifier 7, and fed into the A/D converter 4. At software defined intervals, such as once daily, the microprocessor 1 turns on the A/D converter 4 and takes a sample of voltage from the operational amplifier 7. This value is converted into its corresponding pH value, and stored along with the date in the RAM memory 3. A keypad 11 is used as a user interface with the microprocessor 1 to perform such activities as setting the time, setting the start day of the menstrual cycle, recalling data for different days, etc. The microprocessor, ROM, RAM, A/D converter and LCD controller may be advantagiously combined in a single microcontroller package to save space and power consumption.

Figure 3:
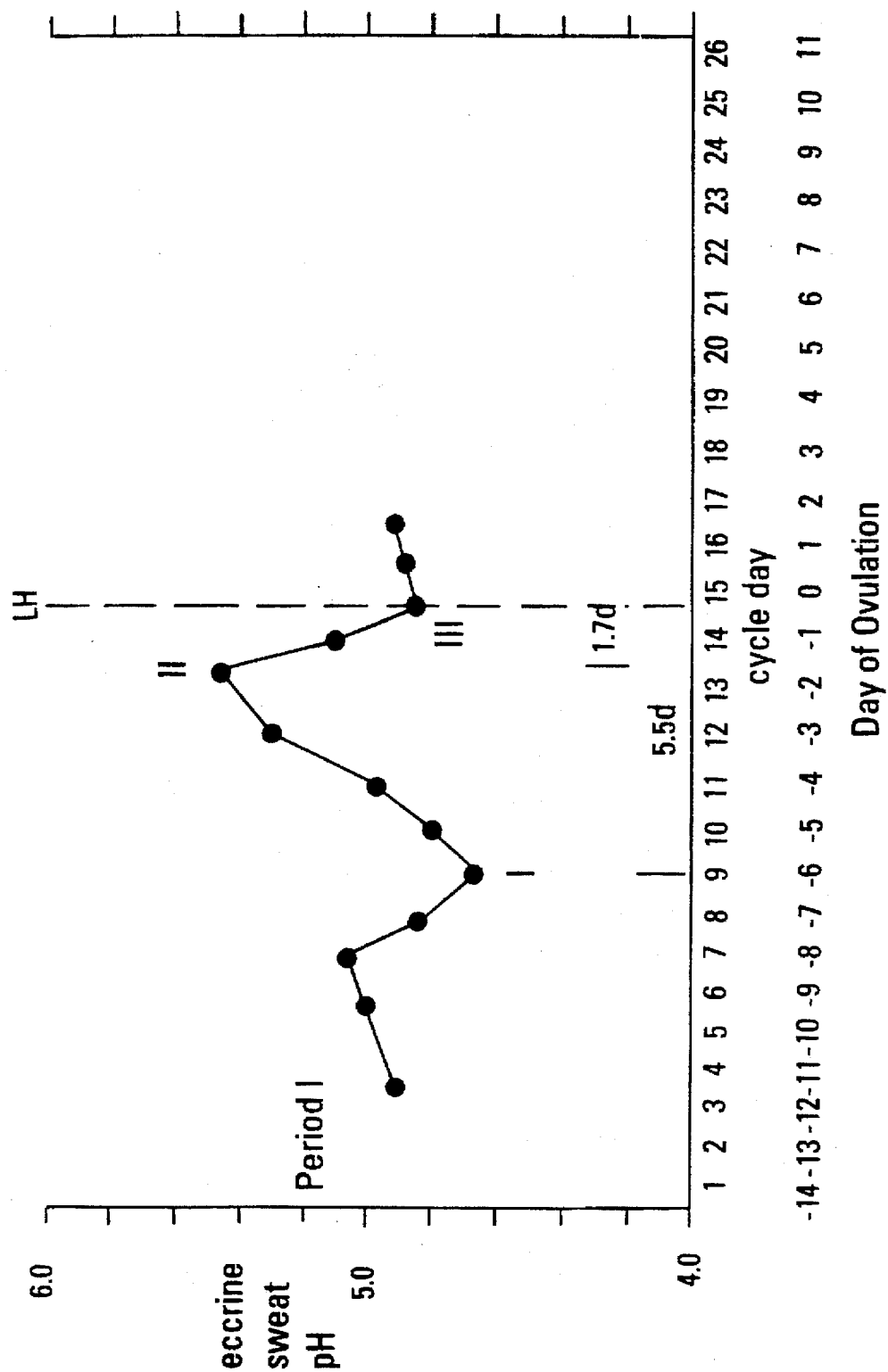
FIG. 3 is a diagram illustrating the pattern of eccrine sweat pH produced in accordance with the method of the present invention.

The readings obtained over the course of the menstrual cycle take the characteristic pattern shown in FIG. 3. The pH readings are somewhat stable for the first several days following the onset of menstruation. The pH values begin to decline around 6 to 9 days prior to the LH surge, reaching a a low point delineated by roman numeral I on average 5–6 days prior to the LH surge. This point is also refered to as the "acid peak" or "nadir". This distinct pH nadir is usually the lowest pH seen up to that point in the cycle. Following this acidic peak, within 1–2 days there is a sharp rise in the pH of greater than 0.3 pH units and in some cases as high a 1 pH unit, which reaches a peak at roman numeral II, on average 1–2 days prior to the LH surge. Finally, this peak shows a decline towards the inital baseline pH level within about 1 day of ovulation.

The task of recording and interpreting the pH data may be accomplished automatically. The instrument is compact, and when worn on wrist the sensor is in constant contact with the skin, thus allowing readings to be taken without user manipulation. Further, the instrument automatically recognizes whether the wrist is present. This is because the device is programmed to accept readings only within a software-defined physiological range, which will not occur if their is no wrist to make a contact bridge between the pH-indicating and reference electrodes. Thus when the device is not worn, the reading sequence is delayed by a software routine until the wrist is present again, allowing the user to wear the device at their leasure, preferably for several hours each day. It is necessary only for the user to set the first day for her menstrual cycle into the memory of the device to reset the cycle day counter, thus initiating the automatic reading cycle.

Figure 4:
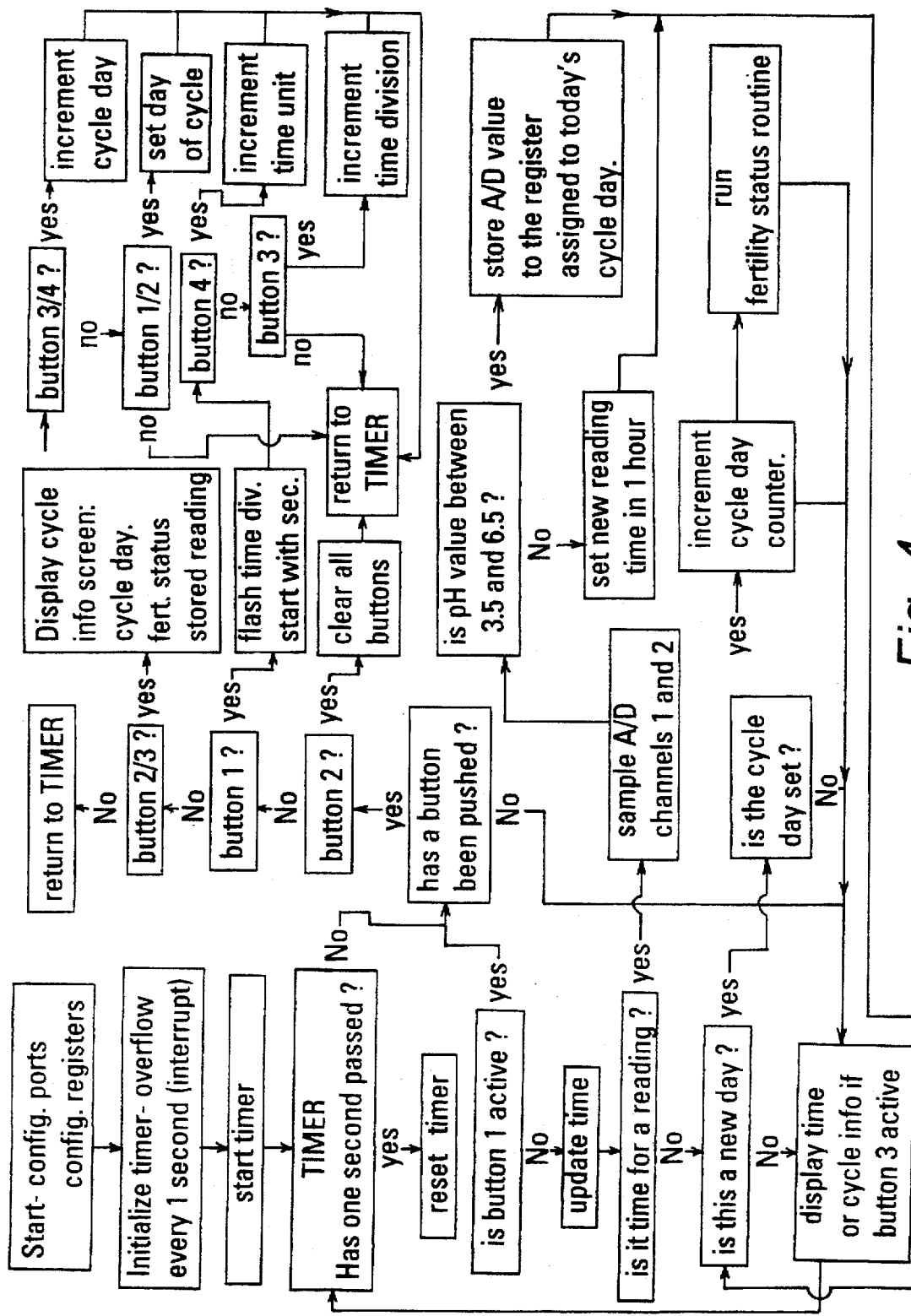
FIGS. 4, 5 and are logic flow charts showing the software algorithms for pattern recognition of eccrine sweat pH values of the present invention.

FIG. 4 illustrates the software flowchart for running the device, and for monitoring and interpreting these pH changes described above. This software routine may be summarized as follows. At the start of the program, the microprocessor is initialized, followed by the configuring of the ports and registers. The microprocessor timer circuit is initialized, and set to count every second. Once the timer is started, the main routine begins to cycle, which on every second passing updates the time. The routine also waits for a keypad entry, or the time when a reading must be taken. If a button is pressed, a subroutine searches for the button which is active and performs the appropriate function. When button 1 is pressed, the timer is halted and the seconds flash, indicating that the time is to be set. Pushing button 3 flashes the next time division at each push, ie. minutes, hours, days, months, then back to seconds. Pushing button four increments the corresponding time division. Pushing button 2 clears all buttons which are active and returns to the main routine. Buttons 2 and 3 pushed simultaniously changes from the main viewing screen, which displays time and fertility status, to the reading screen, which displays the fertility status, cycle day and reading stored for that cycle day. This mode is used for setting the first day of the menstrual cycle, for looking up the present cycle day, or for viewing previously stored readings. The first day of the menstrual cycle is set in this mode by pushing buttons 3 and 4 simultaniously, which increments a visual counter on the screen called the cycle day counter. Pushing these buttons repeatedly until the number 01 appears put the counter on menstrual day 1. Pushing buttons 1 and 2 simultaniously after this resets the counter, and it keeps track of the cycle day thereonafter. The cycle day counter can be reset on any day early in the cycle (ie. before day 5), as long as the correct day is entered. This initializes the A/D sampling of the probe, which then occurs automatically every day at a predefined time. Assuming that the wearer has worn the device for several hours when the reading occurs, the probe will be stable and can be sampled rapidly (ie. in less than 1 second). advantagiously, several readings may be performed in succession and the average value stored. If the pH value read is above pH 6.5 or below pH 3.5, the device enters a subroutine which does not store the reading but resets the reading time to the next hour. In this manner the device avoids recording erronious values which may occur if the sensor is improperly seated on the wrist or if the device is not worn altogether.

Figure 5:
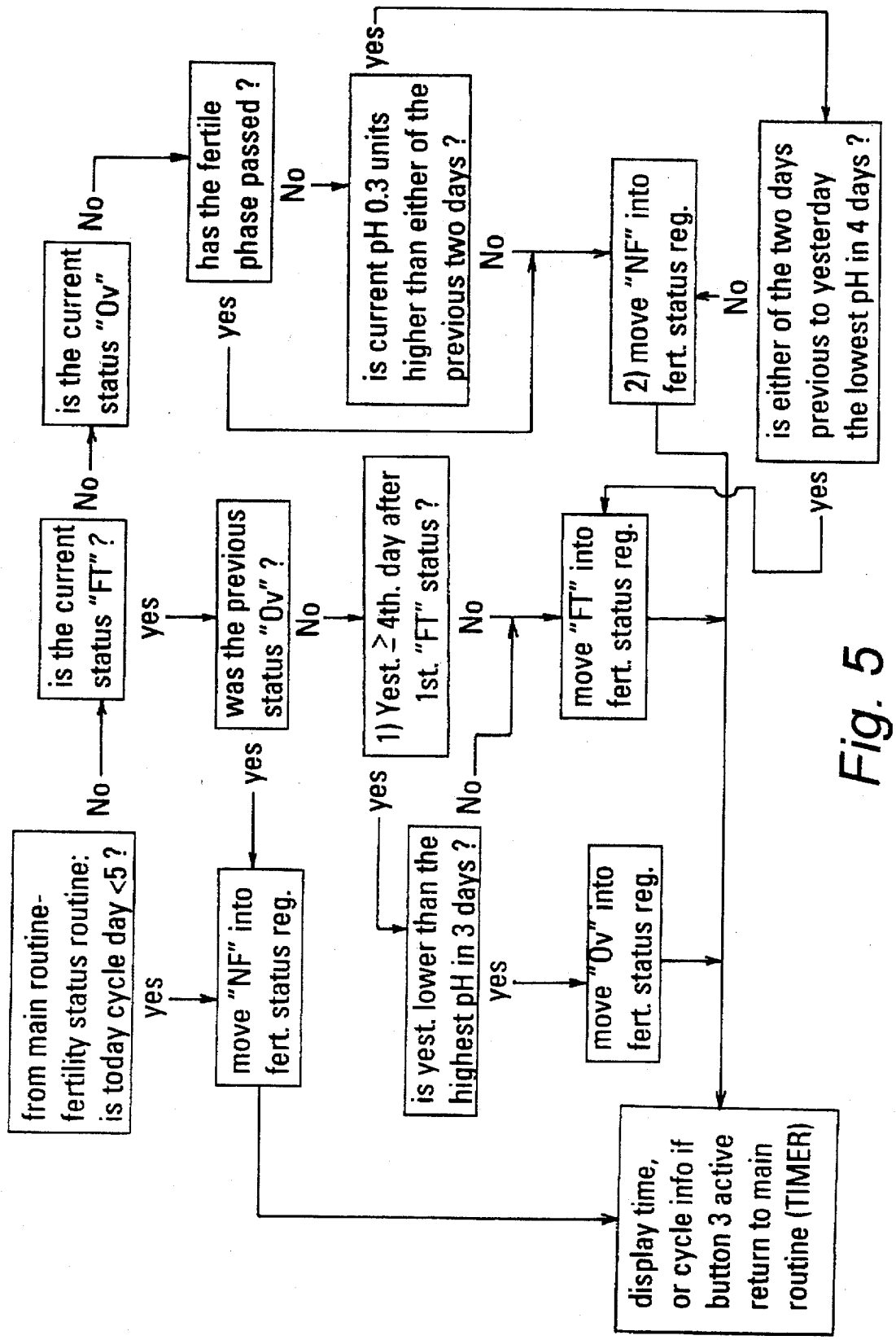
Figure 6:
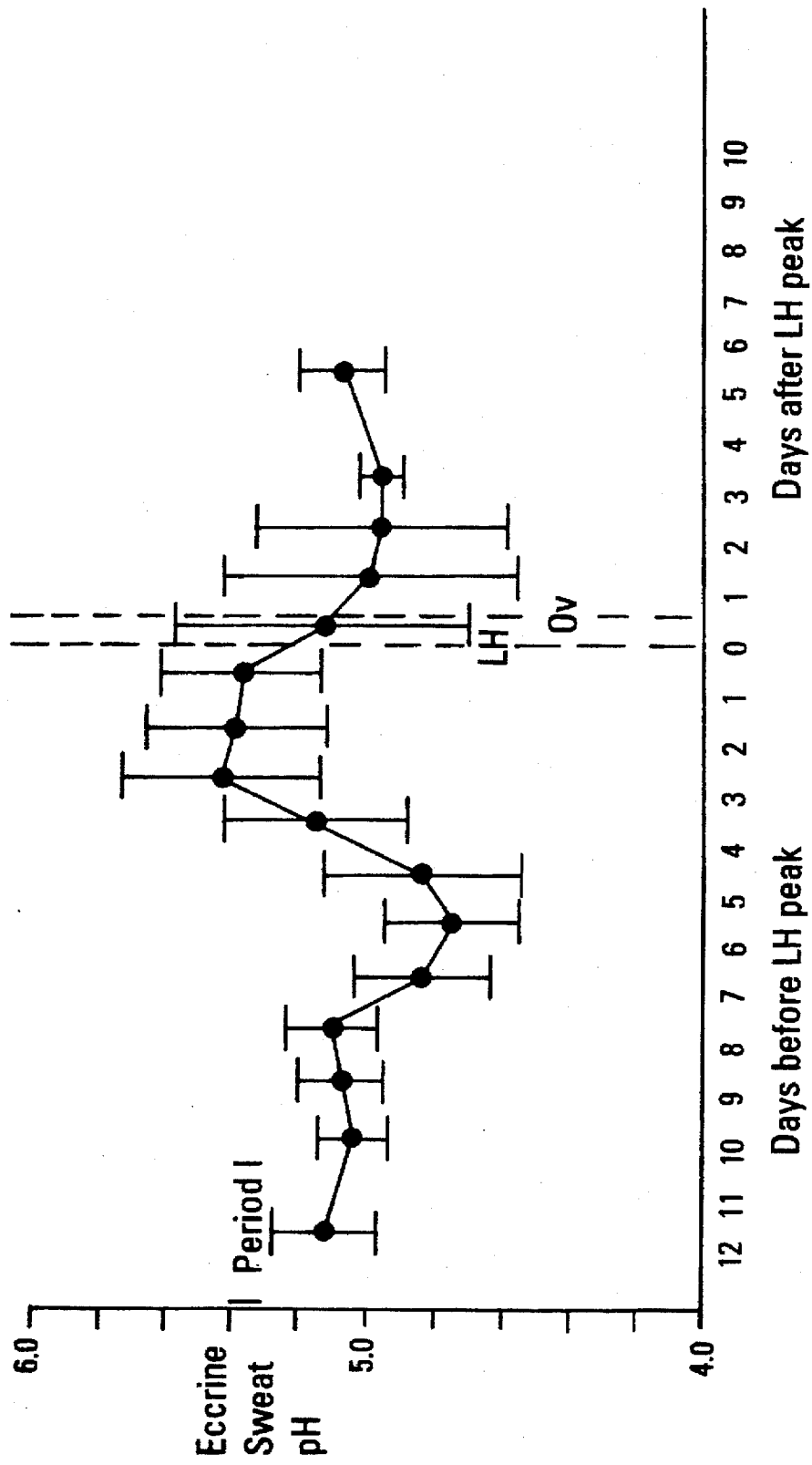
FIG. 6 is a diagram illustrating the average pattern of eccrine sweat pH for spontaniously ovulating women based on 6 menstrual cycles.

For the purposes of this invention, there are three fertility status levels defined. The first is the not-fertile (NF) phase or state which is the period from the first day of the menstrual cycle to approximately 4 days prior to ovulation. A second not-fertile (NF) phase or state starts approximately 1 day following ovulation to the end of the menstrual cycle. The fertile (FT) phase or state is defined as the period 4 days prior to ovulation until one day after ovulation. The ovulation (Ov) phase or state is defined as the period immediately following the blood LH peak and lasting between 1–2 days. At the end of each day, the device increments the cycle day counter, and then determines the fertility status of the user. This is by using a software algorithm for pattern recognition as shown in FIG. 5. The algorithm assumes a not-fertile (NF) status for days 1-4, and displays this on both the main and reading screens. On day 5 the device begins looking for the peak in eccrine sweat acidity (pH nadir). It does this by looking at the latest pH reading and determining if it is 0.3 pH units higher than one of the previous two days. If this is not true, than NF is displayed and stored with the current reading. If it is true, then the algorithm looks back to see if one of the previous two days was the lowest pH in 4 days. If this is not true, then NF is displayed and stored. If it is true, then the acid peak has passed and this is the first fertile day. A fertile icon "FT" is then displayed and stored with this reading and the three days after that. On the 5th day the algorithm looks back again to determine if the high pH peak (roman number II in FIG. 3) has occured. It determines if the current reading is lower than the highest pH reading in the past 3 days. If this is not true, the peak is most likely the current reading and thus another "FT" is added. If this is true, the peak is passed and this is the LH surge day. Thus an "Ov" is displayed and stored with the reading. The following day, a last "FT" is displayed, followed by a "NF" for all days to the end of the cycle. This algorithm is thus dynamic in that it can lengthen the minimun fertile period if the time between the acid peak and high pH peak is longer than expected.

At any time during the cycle the user can view the fertility status and reading for any cycle day. This is performed by calling the reading screen by pressing buttons 2 and 3 simultaniously, and then incrementing the cycle counter by pressing buttons 3 and 4 simultaniously until the wanted cycle day appears. Upon returning to the main screen, the current cycle day is automatically displayed.

The pH sensing combination electrode is comprised of a pH sensing electrode 13, a reference electrode 14, and a housing 15 which holds them within the same plane. The sensing electrode 14 may be any electrode capable of converting a variable pH into an electronic signal, such as a glass envelope electrode, an ionophoric membrane electrode, a cationic exchanger electrode, etc. Advantagiously the electrode is constructed in such a manner as to require little maintenance such as fluid filling and calibration, and should operate effectively under sparse water conditions. This may be obtained by using a sensing electrode with low water content or a solid state sensing electrode of drift preferably not greater than 1 mV/day. A solid state electrode may be defined for the purposes of this application as one which contains little to no aqueous filling solution or prior hydration. An example of such possible electrode constructions are described as follows:

a) An electrode similar to that described in Banks et.al U.S. Pat. No. 4,814,060 comprised of a housing, a silver/silver chloride wire, an internal filing solution of
  i) 80–90% formamide
  ii) 10–20% $H_2O$
  iii) 0.001–0.1M NaCl
  iv) saturated $AgNO_3$
  v) polyvinyl alcohol for gelling
  vi) a hydroscopic agent
and an $H^+$ sensitive ionophoric membrane covering the open end of the housing comprising
  i) 1% ETH1907 ionophore
  ii) 1% potassium tetrakis (p-chlorophenyl)borate
  iii) 30% polyvinylchloride (PVC),
  iv) 68% dioctyl sebecate as plasticizer alternatively, b) An electrode similar to that described in Ushizawa et.al U.S. Pat. No. 4,582,589 comprising a platinum or carbon substrate insulated on all but one side, the exposed side having its surface coated with a pH sensitive polymer such 1-aminopyrine and pyridine by electrochemical oxidation polymerization.

c) An electrode similar to that described in Yamaguchi et.al. U.S. patent application Ser. No. 5,133,856 comprising an ETH1907 ionophoric membrane, which covers a graphite conducting element which has had deposited on it a reversible redox polymer film.

The reference electrode to accompany the sensing electrode may also be of any standard construction such as a calomel reference electrode, silver/silver chloride reference, etc. but preferably requires no filing of internal solutions and be stable with respect to interfering ions and drying. Examples of such electrodes include:

d) An electrode similar to Murray, et.al U.S. Pat. No. 4,653,499 comprising a solid state non-aqueous electrode consisting of a silver/silver chloride wire coated with a dry layer of crystaline KCl and covered with a membrane of cellulose acetate butyrate.

5) An electrode similar to Banks et.al above but with cellulose acetate butyrate membrane instead of an ionophoric membrane.

A non-solid state pH sensitive ionophoric membrane may be used with a calomel reference electrode as long as provision is made to prevent the electrodes from drying. An example of this arrangement is described in example 1.

EXAMPLE 1

A pH sensing ionophoric membrane electrode was constructed by making up a solution of 167 mg of polyvinylchloride (PVC), 385 mg of dioctyl sebecate, 6 mg potassium tetrakis (p-chlorophenyl)borate, and 6 mg of ETH1907 ionophore in 4 mL of tetrahydrofuran (THF). This solution was cast in a 4 cm diameter petri dish, and the resulting membrane after evaporation was cut to 1.5 cm in diameter and glued to the end of a PVC tube using a saturated solution of PVC in THF. Once dry, this tube was filed with a saturated solution of KCl, and a silver/silver chloride electrode was inserted into the solution. The tube was then closed via a threaded joint and a lead attached to the silver wire through a hole in the top. This electrode was found after hydration to have a potential change of approx. 56 mV/pH division, and was linear in the pH 4 to 7 range. This electrode was used in combination with a standard calomel reference electrode to measure the skin sweat pH of several women by placing the two electrodes within 1 cm of each other on either the palm surface, upper wrist surface or lower wrist surface. The potential difference between the sensing electrode and the probe was amplified using a CA 3240 cmos operational amplifier and the calibrated value was displayed on an LCD screen using a 7106 LCD controller. The sensing electrode was calibrated using standard pH buffer solutions prior to each reading. The readings at the three sites of each woman was averaged for the day, and readings were taken almost every day during their menstrual cycle. The pH readings for six menstrual cycles from 4 women are shown in FIG. 4. As can be seen from the figure, in all of the women tested there was a significant acidification of on average 0.4 pH units approximately 5.5 days (SD=±0.4 days) prior to their LH peak measured using standard urinary assays for LH. This acidification was in all cases followed by a significant alkalinization of on average 0.7 pH units which peaked 1.7 days (SD=±0.79 days) prior to the LH peak and which corresponds closely with the expected blood peak in total estrogens. A second rapid acidification of on average 0.4 pH units occured at the approximate time of ovulation, plateauing on average 13 hours following the urinary LH peak (SD=±5.4 hours).

While a certain illustrative method and apparatus embodying the present invention has been shown in the drawings and described above in considerable detail, it should be understood that there is no intention to limit the invention to the specific forms and embodiments disclosed. On the contrary, the intention is to cover all modifications, alternative constructions, equivalents, methods and uses falling within the spirit and scope of the invention as expressed in the appended claims.

What is claimed is:

1. A method for determining the fertility status of a female human, comprising monitoring the day to day changes in the eccrine sweat pH of the said female human, and ascertaining the fertility status of the said human from the pattern of pH change observed.

2. A method for determining the fertility status of a female human during her menstrual cycle, comprising monitoring the eccrine sweat pH cycle of the said female human daily, and ascertaining the start of the fertile period as the first day of a rise in pH of at least 0.3 pH units following a distinct pH nadir.

3. A method as claimed in claim 2, where the eccrine sweat is collected from the human female's skin surface before its pH is measured.

4. A method as claimed in claim 1, where the fertile state of ovulation is ascertaining to have occured aproximately 5.5 days following a distinct pH nadir.

5. A method as claimed in claim 4, where the eccrine sweat is collected from the human female's skin surface before the pH is measured.

6. A method as claimed in claim 1, where the fertile state of ovulation is ascertained to have occured approximately 4 days after the first day of a rise in pH of at least 0.3 pH units following a distinct pH nadir.

7. A method as claimed in claim 6, where the eccrine sweat is collected from the human female's skin surface before the pH is measured.

8. A method as claimed in claim 1, where the eccrine sweat is collected from the human female's skin surface before the pH is measured.

9. A device for determining the fertility status of a female human comprising a means for sensing eccrine sweat pH values, a means for mounting said sensor in intimate contact with the female subject's skin, and a means for displaying said pH values and a means for indicating when said pH values correspond to a predetermined pattern, such pattern indicative of the fertility status of the subject.

10. A device as claimed in claim 9, wherein said predetermined pattern of pH values comprises a current daily pH value higher than one of previous two days values by at least 0.3 pH units, one of the previous two days values being the lowest pH value of at least the last 3 days, indicating the onset of the fertile state.

11. A device as claimed in claim 9, wherein said predetermined pattern of pH values comprises a current daily pH value occuring at least 4 days following the onset of the fertile state pattern which is lower than the highest pH of the previous 3 days, indicating the onset of ovulation.

12. A device for determining the fertility status of a female human, comprising
 a) a read only memory means for storing a diagnostic program for determining the fertility state of the female subject from eccrine sweat pH data values;
 b) an erasable memory means for storing the daily eccrine sweat pH data values;
 c) a display means for displaying the characters representing the fertility state;
 d) a sensing means for sensing the eccrine sweat pH of a subject and outputing corresponding analog signals;
 e) a conversion means for converting said analog signals to digital signals;
 f) an input means enabling the inputing of data by the female subject;
 g) a microprocessor means for controlling the processing of data with said diagnostic program, said microprocessor means being connected to read only memory means, erasable memory means, display means, conversion means and input means, wherein said diagnostic program comprises algorithms for the recognition of predetermined patterns of data values, said algorithms being applied to said current daily data value and said stored daily data values by said microprocessor means, said microprocessor means controlling said display means to display characters representing one of several fertility states of said subject in response to recognition of a corresponding one of said predetermined patterns.

13. A device for determining the fertility status of a female human as claimed in claim 12, wherein said diagnostic program comprises first and second algorithms for the recognition of first and second patterns of data values, said first pattern being that the current daily pH value is higher than one of previous two days values by at least 0.3 pH units, one of the previous two days values being the lowest pH value of at least the last 3 days, said second pattern being that the current daily pH value occuring a at least 4 days following the first pattern is lower than the highest pH of the previous 3 days.

14. A device as claimed in claim 12, wherein said sensing means comprises a pH indicating electrode of large surface area and a reference electrode.

15. A device as claimed in claim 12, wherein said sensing means comprises a solid state pH indicating electrode and solid state reference electrode.

16. A device as claimed in claim 12, wherein said sensing means comprises a pH indicating electrode utilizing an ionophoric membrane.

17. A device as claimed in claim 12, wherein said device possesses means of being strapped to the skin of the subject, such that the sensing means contacts the skin.

* * * * *